United States Patent [19]

Wichterle

[11] Patent Number: 4,846,832

[45] Date of Patent: Jul. 11, 1989

[54] SOFT AND ELASTIC INTRACAMERAL LENS AND A METHOD FOR MANUFACTURING THEREOF

[75] Inventor: Otto Wichterle, Praha, Czechoslovakia

[73] Assignee: Ceskoslovenska Akademie Ved., Czechoslovakia

[21] Appl. No.: 60,771

[22] Filed: Jun. 10, 1987

Related U.S. Application Data

[63] Continuation of Ser. No. 680,479, Dec. 11, 1984, abandoned.

[30] Foreign Application Priority Data

Dec. 12, 1983 [CS] Czechoslovakia .................... 9329-83

[51] Int. Cl.$^4$ .......................... A61F 2/16; B29D 11/00
[52] U.S. Cl. ......................................... 623/6; 264/1.1; 264/2.6; 264/319
[58] Field of Search ..................... 623/6; 264/1.1, 2.6, 264/299, 319

[56] References Cited

U.S. PATENT DOCUMENTS

| | | | |
|---|---|---|---|
| 4,172,297 | 10/1979 | Schlegel | 623/6 |
| 4,424,597 | 1/1984 | Schlegel | 623/6 |
| 4,449,257 | 5/1984 | Koeniger | 623/6 |
| 4,556,998 | 12/1985 | Siepser | 623/6 |
| 4,642,114 | 2/1987 | Rosa | 623/6 |

OTHER PUBLICATIONS

"The Soft Intraocular Implant", by K. R. Merta et al., The Cornea in Health & Disease (VIth Congress of The European Society of Ophthalmology), Royal Society of Medicine International Congress & Symposium Series No. 40, published jointly by Academic Press, Inc. (London), Ltd. and Tue Royal Society of Medicine, Aug. 1981, pp. 859–863.

*Primary Examiner*—Ronald L. Frinks
*Attorney, Agent, or Firm*—Leydig, Voit & Mayer

[57] ABSTRACT

A soft and elastic intracameral lens, the back surface of which is formed by a continuous rotation-symmetric convex surface and the front surface comprises a central convex surface of sphere or quadric rotation-symmetric body linked on the diameter of 4 to 8 mm, preferably through a rounded transition, to a concave ring surface of a sphere or a toroid, whereas the distance between the concave ring surface and the back surface is 0.05 to 1.5 mm.

The intracameral lens according to the invention is manufactured by charging a mold, which has the negative shape of the required front surface of the lens and is provided at the periphery with a sharp edge protruding by 0.05 to 1.5 mm above the end of the peripheral ring surface, with a monomer mixture as high as above the sharp edge to form a continuous convex meniscus and the mold with the monomer mixture is then exposed to polymerization conditions.

17 Claims, 1 Drawing Sheet

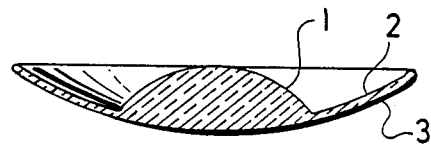
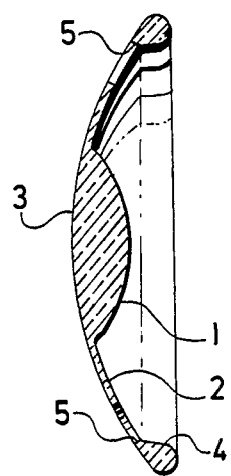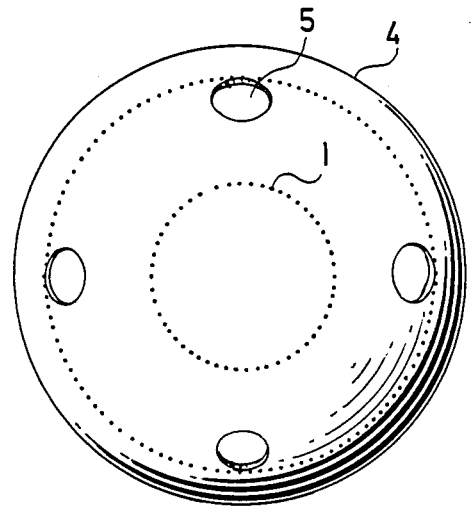
FIG. 2  FIG. 3
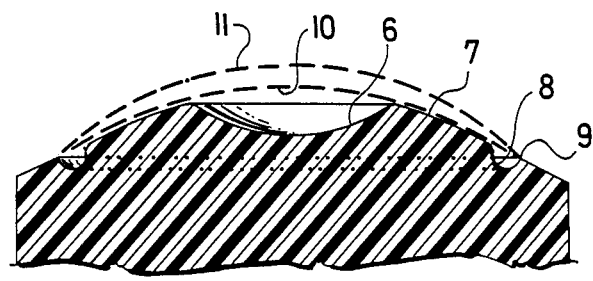
FIG. 4

SOFT AND ELASTIC INTRACAMERAL LENS AND A METHOD FOR MANUFACTURING THEREOF

This application is a continuing application of application Ser. No. 680,479, filed Dec. 11, 1984, now abandoned.

The invention pertains to a soft and elastic intracameral lens and to a method for the production of it.

The soft intracameral lens made from a hydrophilic synthetic gel, known from the Czechoslovak Patent Application No. 1026-83, is very similar to the natural lens of the eye both by the shape and refractive index and may replace it in a cataract operation. Application of this lens is limited to cases when the operation technique leaves, after removing the turbid eye lens, a sound rear capsula lentis, which is able to hold the lens in a central position. However, the capsula is injured in many cases and the lens according to the aforesaid invention in some instances cannot be used because, even after fixation of the lens with stitches, the risk remains that the lens will fall deeper into the posterior chamber of the eye.

The present invention pertains to a soft and elastic intracameral lens, which has its edge adapted for reliable fixation in the eye in close proximity of the angula iridis, and the shape of which does not allow the lens after fixation to bear on the iris. The convex back surface of the lens according to the invention is formed by a rotation-symmetric surface, advantageously corresponding by its shape to a convex meniscus of liquid, and the front surface which has, in its central part, the shape of a spherical cap or a cap of the quadric surface of revolution, whereas this cap links to a concave ring surface, which terminates the lens on its edge so that it is distanced by 0.05 to 1.5 mm from the front surface and this distance thus takes up the edge thickness of the lens. The edge ring does not have an optical function and it may therefore be arbitrarily shaped in a detailed performance. For example, stronger sites can be made in this ring, advantageously as a circular thicker barrier, which may serve for introduction of stitches for the fixation of the lens. To make the introduction of stitches easier, holes may be provided in the peripheral ring of the lens.

Another objective of this invention is a method for manufacturing this lens, which is based on polymerization casting in open molds, which are enclosed by a sharp circular edge and the bottom of which are enclosed by a sharp circular edge and the bottom of which has a negative shape of the front surface of the above described lens. A monomer mixture able to polymerize is piled up into the convex meniscus above this edge, before it is brought to higher temperature or irradiated. The height of the sharp edge above the circumference of the mold bottom determines the desired thickness of the lens edge (0.05 to 1.5 mm). The convexity of the meniscus can be varied within certain limits by the amount of charged mixture and this varies, at the same time, the central radius of curvature and thus also the refractive power of the lens. Therefore, a great number of molds with various radii of the central cavity is not necessary for casting these lenses. Four to five types of molds with different curvatures of the central cavity will be enough and any fine interpolation between the refraction limits of lenses cast in an individual mold can be obtained by fine grading of the charged amount.

The production of lenses according to the invention by the casting of a monomer mixture is particularly advantageous for the lenses manufactured from hydrophilic materials. The monomers mentioned in the U.S. patents of the following numbers can be considered: U.S. Pat. Nos. 2,976,576; 3,220,960; 3,937,680; 3,948,871; 3,949,021; 3,983,083; 3,988,274; 4,018,853; 3,875,211; 3,503,942; 3,532,679; 3,621,079; 3,639,524; 3,700,761; 3,721,657; 3,758,448; 3,772,235; 3,786,034; 3,803,093; 3,816,571; 3,940,207; 3,431,046; 3,542,461; 4,055,378; 4,064,086 and 4,062,627.

In principle, the described lenses can also be produced by machining of xerogel, i.e. by the technique analogous to the production of gel lenses by turning, e.g. according to the Czechoslovak Pat. No. 132, 141.

A replica of the lens is first made in a linearly reduced scale from the hydrophilic material in the form of xerogel and then is allowed to swell in physiologic saline. However, this method is probably economically less suitable in comparison to the casting of a monomer mixture in open molds.

The gels obtained by polymerization of monomer mixtures containing 2-hydroxyethyl methacrylate (HEMA) as a main polymerizable component are especially suitable for this application. The gels employed in the present invention when placed in contact with water, after reaching equilibrium swell to contain at least 20% water. The gels take up only 40% water by swelling and have therefore a relatively high refractive index (1.42 to 1.43). Consequently, only a relatively low central radius of the front surface (about 4 mm) suffices to achieve the required refraction 15 to 25 diopter in the immersion of a vitreous body and the total thickness of the lens is relatively small. In addition, the HEMA gels comprise long-term, successfully tested materials for eye prostheses and surgery.

The lenses according to the invention made from silicone materials may be also produced by casting in open molds, for example, by the polymerization of octamethylcyclotetrasiloxane. They may be, however, advantageously manufactured by pressure molding in closed molds.

The intracameral lenses according to the invention may be additionally finished, e.g. by dyeing or pigmenting of the peripheral ring by known methods. The ring of lenses from the soft hydrophilic materials can be dyed, after covering the optical zone, with direct dyes which have proved suitable for contact gel lenses. Shades as dark as possible are preferably chosen, because the reason for this finish is to exclude all undesirable reflections coming from the periphery of the optical zone. A suitable method of finish consists, for example, in the successive impregnation of the peripheral ring of the lens with a solution of silver nitrate and a solution of ammonium sulfide, which forms a black pigment of silver sulfide inside the ring.

The invention is further illustrated in diagrammatic drawings and an example.

FIGS. 1 and 2 display an intracameral lens in an axial sectional view;

FIG. 3 shows the lens according to FIG. 2 in the front view; and

FIG. 4 shows a sectional view on a casting mold for manufacturing the lenses according to FIGS. 2 and 3.

The front surface of a lens of basic shape (FIG. 1) consists of a convex central part 1, linked to a toroidal concave surface of a peripheral ring 2. The spherical convex central part 1 may, for example, have a diameter from 4 to 8mm. The back surface 3 has a spherical convex shape. According to FIGS. 2 and 3, the front surface consists of a central part 1 with the shape of a convex ellipsoid of revolution having the longer semiaxis in the axis of the lens and a peripheral ring 2 of this surface having the shape of a common toroid, which ends in a circular barrier 4. Circular openings 5 are formed n the peripheral ring 2 in close proximity of the barrier.

The casting mold (FIG. 4) for manufacturing the lenses has functional casting surfaces 6, 7 and 8 corresponding to the surfaces 1, 2 and 4 of the cast lens. The circumference of the cast lens is demarcated with a sharp edge 9. A larger or smaller amount of monomer mixture can be piled up above the edge, as indicated by two dashed curves of meniscus meridians 10 and 11). Nothing corresponding to the openings 5 in the lens occurs on the casting mold. These openings 5 are formed first after casting the lens.

EXAMPLE

The given real example concerns manufacturing lenses from a HEMA gel by casting the monomer mixture which contains 80 weight parts HEMA, 0.5 part ethylene dimethacrylate, 20 parts glyceral, and 0.5 part diisopropyl percarbonate. This mixture (0.1 g) is charge into polypropylene molds corresponding by shape to FIG. 4, where their central spherical concave surface 6 of radius 4 mm reaches as far as to the diameter of 5.5 mm, the peripheral ring 7 has the shape of a convex totoid, which forming (meridian) circle has the diameter 6.8 mm and the distance of its center from the axis is 2.4 mm. A rounded circular groove 8 is formed in the edge of the ring, which reaches 0.5 mm below the toroidal curve and gets up to the sharp circular edge 9 of diameter 7.5 mm reaching 0.5 mm above the toroidal curve.

The charged molds are inserted in a strictly horizontal position into a chamber filled with pure nitrogen and heated to 60° C. After 30 minutes the molds containing polymer moldings are placed in water, where the moldings swell with water and are spontaneously released from the molds. Three to six symmetrically placed openings are made near the thicker peripheral ring by forcing a sharp punch, with a cutting-edge having a diameter of 1.5 mm, through the lens against a base of hard rubber. A black pigmenting of the peripheral edge is then obtained by clamping the central optical part between tightly covering Teflon masks and immersing the peripheral ring first into a 10% solution of silver nitrate in 10% ammonia for 30 minutes and then, after short rinsing with water, into a 5% solution of ammonium sulfide. The lenses are eventually repeatedly thoroughly washed with boiling water and sterilized in physiologic saline.

I claim as follows:

1. A soft, elastic intracameral lens comprising:
   (a) a back surface having a continuous rotation, symmetrical form in the shape of a convex meniscus of liquid, and
   (b) a front surface which consists (i) of a convex surface at its center and (ii) a peripheral ring surface about the central convex surface, the central convex surface being in the form of a sphere or quadrically rotated symmetrical body, and the peripheral ring surface being in the form of a concave spherical or toroidal ring having a thickness of 0.05 to 1.5 mm.

2. The lens according to claim 1 wherein the central convex surface is linked to the peripheral ring through a rounded transition and the central convex surface has a diameter of 4 to 8mm.

3. The lens according to claim 1 wherein a circular barrier protrudes from the peripheral ring at its outer circumference and exceeds the thickness of the ring by 0.2 to 1.5 mm.

4. The lens according to claim 1 wherein openings of diameter 0.5 to 2 mm are formed between the edge of the lens and its central convex surface.

5. The lens according to claim 1 wherein the lens is made from a hydrophilic lightly crosslinked gel, which contains at least 20% of water in the state of equilibrium swelling.

6. The lens according to claim 1 wherein the lens is manufactured from a crosslinked copolymer, a main component of which is 2-hydroxyethyl methacrylate.

7. The lens according to claim 1 wherein the lens is made from a transparent silicone rubber.

8. The lens according to claim 1 wherein the concave ring of the lens is dyed or pigmented in a dark shade.

9. A soft, elastic intracameral lens comprising:
   (a) a back surface having a continuous rotation, symmetrical form in the shape of a convex meniscus of liquid, and
   (b) a front surface which consists, at its center, of a convex surface and a peripheral ring surface about the central convex surface, the central convex surface being in the form of a sphere or quadrically rotated symmetrical body, and the peripheral ring surface being in the form of a concave spherical or toroidal ring having a thickness of 0.05 to 1.5 mm;
   wherein the front and back surfaces are formed by a polymerization casting process using an open mold, the process comprising:
   (1) charging the mold with a sufficient quantity o a monomer to create a continuous convex meniscus to form the back surface, said mold having the negative shape of the front surface of the lens, and a sharp edge at the periphery of the mold protruding 0.05 to 1.5 mm above the end of the peripheral ring surface; and
   (2) polymerizing the monomer by exposing the mold, after charging, to polymerization conditions.

10. A soft, elastic intracameral lens comprising
    (a) a back surface having a continuous rotation, symmetrical form in the shape of a convex miniscus of liquid, and
    (b) a front surface which consists (i) of a convex surface at its center and (ii) a peripheral ring surface about the central surface, the central surface being in the form of a quadrically rotated symmetrical body, said front surface having a greater curvature than said rear surface and the peripheral ring surface being in the form of a concave spherical or toroidal ring having a thickness of 0.05 to 1.5 mm.

11. The lens according to claim 10 wherein a circular barrier protrudes from the peripheral ring at its outer circumference and exceeds the thickness of the ring by 0.3 to 1.5 mm.

12. The lens according to claim 10 wherein openings of diameter 0.5 to 2 mm are formed between the edge of the lens and its central convex surface.

13. The lens according to claim 10 wherein the lens is made from a hydrophilic lightly crosslinked gel, which contains at least 20% of water in the state of equilibrium swelling.

14. The lens according to claim 10 wherein the lens is manufactured from a crosslinked copolymer, a main component of which is 2-hydroxyethyl methacrylate.

15. The lens according to claim 10 wherein the lens is made from a transparent silicone rubber.

16. The lens according to claim 10 wherein the concave ring of the lens id dyed or pigmented in a dark shade.

17. The lens according to claim 10 wherein the central convex surface is linked to the peripheral ring through a rounded transition and the central convex surface has a diameter of 4 to 8 mm.

* * * * *